United States Patent
Connelly et al.

(10) Patent No.: US 6,579,440 B2
(45) Date of Patent: Jun. 17, 2003

(54) REPLACEABLE REFERENCE JUNCTION INCLUDING AN ION-BARRIER FOR AN ELECTROCHEMICAL SENSOR

(75) Inventors: John P. Connelly, Foxboro, MA (US); Michael M. Bower, Wareham, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 09/884,335

(22) Filed: Jun. 19, 2001

(65) Prior Publication Data

US 2002/0189944 A1 Dec. 19, 2002

(51) Int. Cl.[7] .................... G01N 27/40; G01N 27/333; G01N 27/401
(52) U.S. Cl. ............... 205/775; 204/416; 204/419; 204/433; 204/435; 205/787.5
(58) Field of Search ................... 204/416, 435

(56) References Cited

U.S. PATENT DOCUMENTS

| | | | |
|---|---|---|---|
| 2,886,771 A | * | 5/1959 | Vincent |
| 2,943,028 A | * | 6/1960 | Thayer et al. |
| 3,188,285 A | * | 6/1965 | Watanabe et al. |
| 3,431,182 A | * | 3/1969 | Frant |
| 4,282,081 A | * | 8/1981 | Arrance |
| 4,310,400 A | * | 1/1982 | Mark et al. |
| 4,401,548 A | | 8/1983 | Brezinski |
| 4,447,309 A | * | 5/1984 | Morioka et al. |
| 4,495,052 A | | 1/1985 | Brezinski |
| 4,495,053 A | | 1/1985 | Souza |
| 4,891,124 A | * | 1/1990 | Rigdon et al. |
| 5,470,453 A | | 11/1995 | Nipkow et al. |

OTHER PUBLICATIONS

Brezinski, Donald P. "Use of Half–Cells Barrier to Eliminate Junction Clogging Thermal Hysteresis in Silver/Silver Chloride References Electrodes". Analytica Chimica Acta 134 (1982) : 247–262.

* cited by examiner

Primary Examiner—T. Tung
(74) Attorney, Agent, or Firm—David Barron, Esq.; Richard L. Sampson, Esq.

(57) ABSTRACT

A reference junction for a reference half-cell, the reference junction including an ion-barrier membrane and being sized and shaped for removable receipt within a receptacle of a reference half-cell housing. The reference junction may be included in an electrochemical potential measurement sensor for use in making pH, other selective ion activity, oxidation-reduction potential, and other electrochemical potential measurements.

37 Claims, 8 Drawing Sheets

US 6,579,440 B2

REPLACEABLE REFERENCE JUNCTION INCLUDING AN ION-BARRIER FOR AN ELECTROCHEMICAL SENSOR

BACKGROUND OF THE INVENTION (1) Field of the Invention

The present invention generally relates to electrochemical sensors and more particularly to reference half-cells for use in pH, oxidation/reduction potential, and selective ion activity measurements.

(2) Background Information

Electrochemical potential measurements are commonly used to determine solution pH, other selective ion activities, ratios of oxidation and reduction activities, as well as other solution characteristics. A pH/ion selective electrode/oxidation reduction potential meter (hereafter referred to as a pH/ISE/ORP meter) is typically a modified voltmeter that measures the electrochemical potential between a reference half-cell (of known potential) and a measuring half-cell. These half-cells, in combination, form a cell, the electromotive force (emf) of which is equal to the algebraic sum of the potentials of the two half-cells. The meter is used to measure the total voltage across the two half-cells. The potential of the measuring half-cell is then determined by subtracting the known potential of the reference half-cell from the total voltage value.

The measuring half-cell typically includes an ion selective material such as glass. The potential across the ion selective material is well known by those of ordinary skill in the art to vary in a manner that may generally be described by the Nernst Equation, which expresses the electrochemical potential as a logarithmic function of ion activity (thermodynamically corrected concentration). A pH meter is one example of a pH/ISE/ORP meter wherein the activity of hydrogen ions is measured. pH is defined as the negative logarithm of the hydrogen ion activity and is typically proportional to the measured electrochemical potential.

FIG. 1 is a schematic of a typical, prior art arrangement 20 for measuring electrochemical potential. Arrangement 20 typically includes a measuring half-cell 30 and a reference half-cell 40 immersed in a process solution 24 and connected to an electrometer 50 by connectors 38 and 48, respectively. Measuring half-cell 30 and reference half-cell 40 are often referred to commercially (as well as in the vernacular) as measuring electrodes and reference electrodes, respectively. Electrometer 50 functions similarly to a standard voltage meter in that it measures a D.C. voltage (electrochemical potential) between measuring half-cell 30 and reference half-cell 40. Measuring half-cell 30 typically includes a half-cell electrode 36 immersed in a half-cell electrolyte 32, which is typically a standard solution (e.g., in pH measurements). For some applications, such as pH measurement, measuring half-cell 30 also includes an ion selective material 34. Alternately, when measuring ORP the half-cell electrode 36 is immersed directly into the process solution 24.

The purpose of the reference half-cell 40 is generally to provide a stable, constant (known) potential against which the measuring half-cell may be compared. Reference half-cell 40 typically includes a half-cell electrode 46 immersed in a half-cell electrolyte 42 (FIG. 1). As used herein, the term "half-cell electrode" shall refer to the solid-phase, electron-conducting material in contact with the half-cell electrolyte, at which contact the oxidation-reduction reaction occurs that establishes an electrochemical potential. Half-cell electrolyte 42 (FIG. 1) is hereafter referred to as a reference electrolyte. Electrochemical contact between the reference electrolyte 42 (FIG. 1) and the process solution is typically established through a reference junction 44, which often includes a porous ceramic plug or the like (e.g., porous Teflon®, porous kynar®, or wood) for achieving restricted fluid contact. Ideally, the reference junction 44 is sufficiently porous to allow a low resistance contact (which is important for accurate potential measurement) but not so porous that the solutions become mutually contaminated.

However, for many applications, particularly those having a relatively high ion concentration and/or those at a relatively high temperature, ion contamination is a significant difficulty. Both contamination of the reference electrolyte with process solution components and contamination of the process solution with reference electrolyte components are relatively common. Further, clogging of the reference junction with a variety of contaminants (e.g., process solution salts or silver chloride from the reference electrolyte) is also a relatively common difficulty with typical commercial reference electrodes. Both ion contamination and reference junction clogging may lead to unstable and/or erroneous measurements and therefore tend to be undesirable and problematic.

Turning now to the known art, there are several attempts to overcome the above stated difficulties. For example, U.S. Pat. No. 4,495,052 to Brezinski and U.S. Pat. No. 4,495,053 to Souza (hereafter referred to as the '052 and '053 patents, respectively) disclose reference electrodes having a removable and replaceable reference junction, the reference junction typically consisting of a ceramic plug within a glass tube. The '052 and '053 patents, while possibly providing for improved convenience, do not provide an ion-barrier and therefore do not tend to reduce ion contamination. The reference junctions disclosed therein may also be fragile and prone to breakage during removal and insertion.

Brezinski, in U.S. Pat. No. 4,401,548 (hereafter referred to as the '548 patent) and in Analytica Chemica Acta, 134 (1982) 247–262, discloses a double junction type reference electrode having an internal diffusion barrier between the reference electrolyte and the junction electrolyte. The diffusion barrier consists of a porous glass rod (e.g., Vycor®, manufactured by Corning Glass Works, Corning, N.Y.). Because these reference junctions are porous, their effectiveness tends to be limited, especially at elevated temperatures where the diffusion velocity of ions increases greatly. Further, these reference junctions are disposed in an internal cavity within the reference electrode, which tends to substantially complicate replacement. As such, failure of the reference junction may result in the need to replace the entire reference electrode.

Nipkow, et al., in U.S. Pat. No. 5,470,453 (hereafter referred to as the '453 patent) disclose a double junction type silver/silver chloride reference electrode that features a silver ion reducing agent acting as a silver ion-barrier layer to reduce contamination of the junction electrolyte and reference junction with silver ions and/or silver chloride precipitate. As described above with respect to the '548 patent, these reference junctions are disposed in an internal cavity within the reference electrode and, therefore, tend to be difficult to replace. Further, the reference junction disclosed in the '453 patent is not configured to eliminate migration of process solution components (e.g., ions or other mobile species) into the reference electrolyte. Contamination of the reference electrolyte may therefore be problematic in some applications.

Therefore, there exists a need for an improved reference electrode and/or reference electrode junction for use in pH, selective ion activity, oxidation-reduction potential (ORP), and other electrochemical potential measurements that overcomes the aforementioned difficulties.

SUMMARY OF THE INVENTION

In one aspect, the present invention includes a modular reference junction for a reference half-cell. The reference junction includes a body including a reference electrolyte interface portion, a process solution interface portion, and an internal cavity disposed therebetween. The reference junction further includes an ion-barrier membrane disposed at said reference electrolyte interface portion and is sized and shaped for removable receipt within a receptacle of a reference half-cell housing. In one variation of this aspect, the reference junction includes an ion-barrier membrane shaped substantially in the form of a cylindrical tube and including poly(perfluorosulfonic acid).

In another aspect, this invention includes a reference half-cell. The reference half-cell includes a half-cell electrode, a reference electrolyte, and a reference junction positioned in an outlet for the reference electrolyte, the reference junction being sized and shaped for removable receipt within the outlet. The reference junction includes a junction electrolyte and an ion-barrier membrane disposed between the junction electrolyte and the reference electrolyte. In one variation of this aspect the half-cell electrode includes silver—silver chloride, the reference electrolyte is an aqueous solution including a mixture of potassium chloride and silver chloride, and the ion-barrier membrane includes poly(perfluorosulfonic acid).

In still another aspect, this invention includes an electrochemical potential measurement sensor. The sensor includes a measuring half-cell and a reference half-cell including a half-cell electrode, a reference electrolyte, and a reference junction positioned in an outlet for the reference electrolyte, the reference junction being sized and shaped for removable receipt within the outlet. The reference junction includes a junction electrolyte and an ion-barrier membrane disposed between the junction electrolyte and the reference electrolyte. In one variation of this aspect the measuring half-cell and reference half-cell are mounted in a common housing.

In yet another aspect, this invention includes a method for measuring electrochemical potential. The method includes providing a reference half-cell including a half-cell electrode, a reference electrolyte, and a reference junction positioned in an outlet for the reference electrolyte, the reference junction being configured for selectively inserting and removing from the outlet, the reference junction further including a junction electrolyte and an ion-barrier membrane disposed between the junction electrolyte and the reference electrolyte. The method further includes providing a measuring half-cell, inserting the reference half-cell and the measuring half-cell in a liquid; and electrically connecting the reference half-cell and the measuring half-cell to a voltage meter.

In a further aspect this invention includes a method for fabricating a reference junction for a reference half-cell. The method includes providing a body including a reference electrolyte interface portion, a process solution interface portion, and an internal cavity disposed therebetween, providing an ion-barrier membrane, disposing said ion-barrier membrane at the reference electrolyte interface portion, and sizing and shaping the reference junction for removable receipt within a receptacle of a reference half-cell housing.

DETAILED DESCRIPTION

Figure 1:
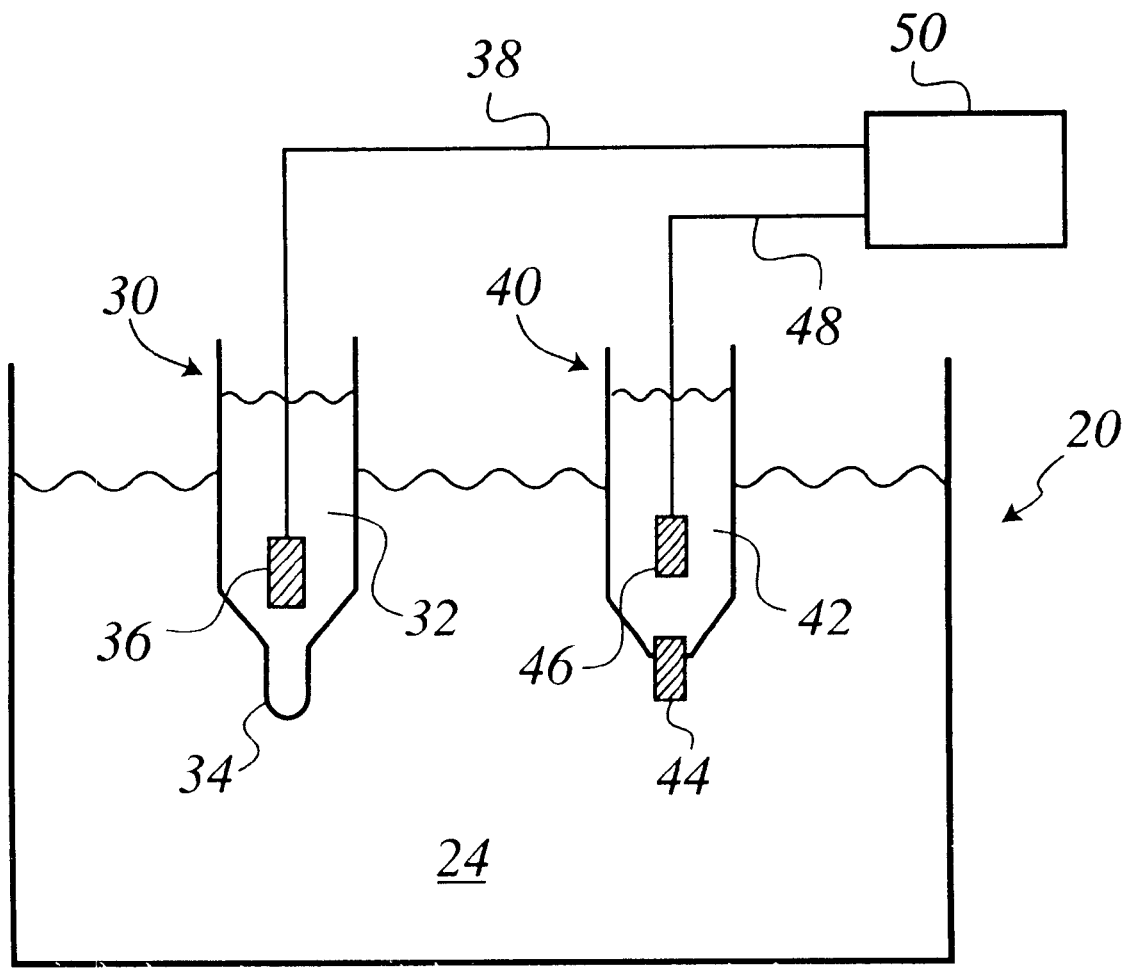
FIG. 1 is a schematic representation of a typical electrochemical potential measurement system.
Figure 2A:
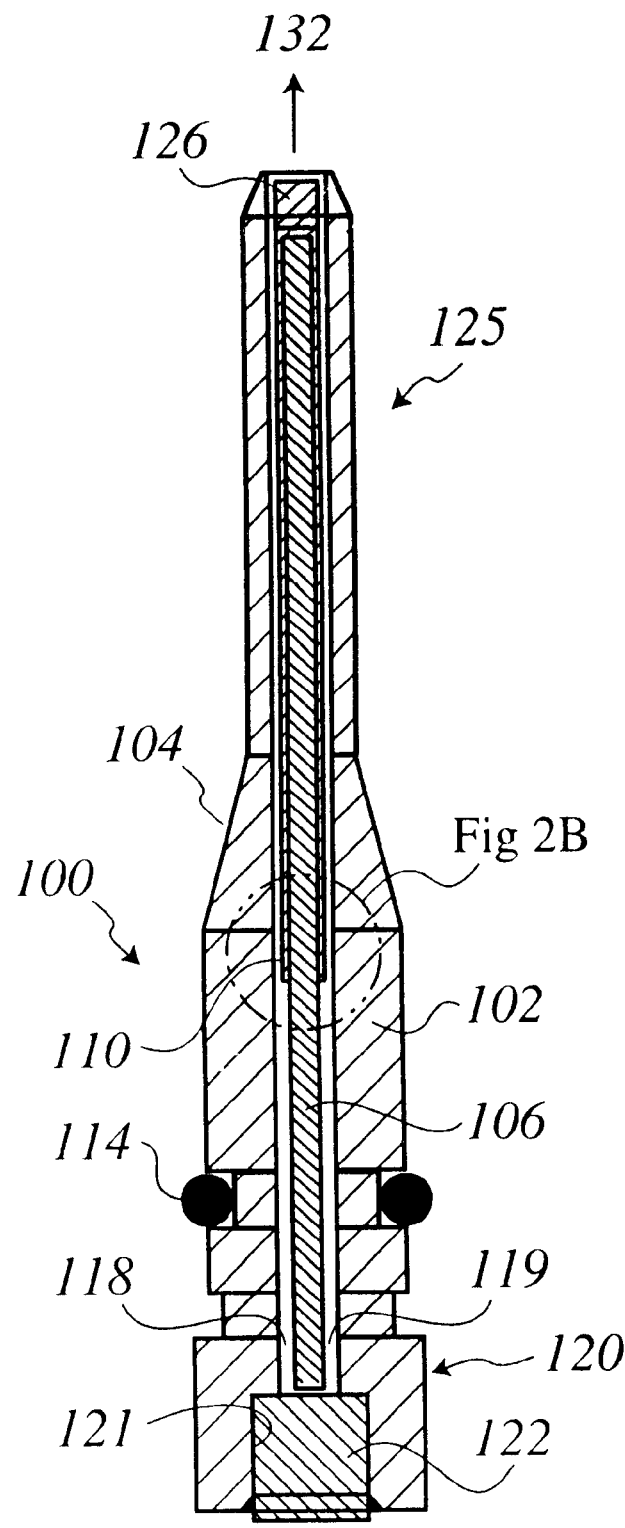
FIG. 2A is a schematic, cross-sectional, representation of one embodiment of a reference junction of the present invention taken along 2A—2A of FIG. 2C.

Referring briefly to FIG. 2A, an apparatus constructed according to the principles of the present invention is shown. Briefly described, the present invention includes a removable and replaceable reference junction 100 for a reference half-cell. Reference junction 100 includes an ion-barrier 110 for preventing ion contamination between a reference electrolyte 42 (FIG. 1) and a process solution 24. The apparatus of this invention may be used in making electrochemical potential measurements in substantially any liquid, but is particularly useful for making pH, other selective ion activity and oxidation-reduction potential measurements.

The present invention is advantageous in that it provides for relatively simple and convenient removal, replacement and/or cleaning of a reference junction used in a reference half-cell and/or electrochemical potential measurement sensor. Further, the reference junction of this invention includes an ion-barrier membrane and provides for substantially reduced ion contamination between a reference electrolyte 42 (FIG. 1) and a process solution 24. Additional advantages of this invention are discussed hereinbelow along with a more detailed description of the invention.

Referring to FIGS. 2A–2D, an exemplary embodiment of the reference junction 100 of this invention is illustrated and described in more detail. Referring initially to FIG. 2A, reference junction 100 includes a body portion 102 (typically constructed of a rigid plastic material) including a reference electrolyte interface portion 125 and a process solution interface portion 120. Portion 120 typically includes a suitably sized and shaped recess 121 with a porous plug 122 (e.g., ceramic) press-fitted therein. Reference junction 100 is configured for insertion into an outlet in a reference half-cell housing (e.g., shown as 214 in FIG. 3A) or an outlet in an electrochemical sensor housing (e.g., shown as 214 in FIG. 4A) along longitudinal direction 132. Reference junction 100 may optionally further include a tapered body section 104 for enabling easy insertion, and a conventional o-ring 114 for effecting a seal between body 102 and the reference half-cell or sensor housing. In use, portion 120 of reference junction 100 is immersed in a process solution 24. Plug 122 provides for restricted fluid contact between the process solution 24 and a junction electrolyte 119 (discussed in more detail hereinbelow).

Reference junction 100 includes a membrane 110 (or film) for providing an ion-barrier between a reference electrolyte 42 (FIG. 1) and a junction electrolyte 119 disposed within an internal cavity 118. In one embodiment, ion-barrier membrane 110 is substantially in the form of a cylindrical tube and is inserted into internal cavity 118. In general, ion-barrier membrane 110 may be made from substantially any ionic exchange material, but is typically made from a cationic exchange film. It is generally desirable that ion-barrier membrane 110 includes a polyanionic material such as polystyrene sulfonic acid, polyacrylic acid, polymethacrylic acid, or poly(perfluorosulfonic acid). Poly (perfluorosulfonic acid) is manufactured and sold as Nafion® by du Pont de Nemours Company Corporation, Wilmington, Del. Membrane 110 advantageously tends to impede the migration of reference electrolyte 42 (FIG. 1) components (e.g., silver ions) into the junction electrolyte 119, which prevents them from precipitating in plug 122 or contaminating the process solution 24. Membrane 110 further tends to impede the migration of process solution 24 components (that may migrate from a process solution 24 through plug 122 and into the junction electrolyte 119) into the reference electrolyte 42 (FIG. 1). Further still, in an exemplary embodiment in which membrane 110 includes Nafion®, it serves as a proton conductor and therefore, provides for a relatively low resistance junction, which tends to provide for stable and accurate potential measurements.

Reference junction 100 also typically includes a wick 106 (e.g., made of paper) that runs the length of internal cavity 118. Wick 106 typically serves multiple functions. First, it acts as a flow constrictor within internal cavity 118, slowing the migration of potential contaminants from a process solution 24. Further, the wick 106 absorbs junction electrolyte 119 (which typically fills internal cavity 118 in use) and therefore, tends to reduce dehydration effects at elevated temperatures. Wick 106 may also effect a seal between ion-barrier membrane 110 and the body 102 (such as a constriction member 134 thereof, shown in FIG. 2B) by swelling upon the introduction of junction electrolyte 119, whereupon the ion-barrier membrane 110 presses against body 102.

Figure 2B:
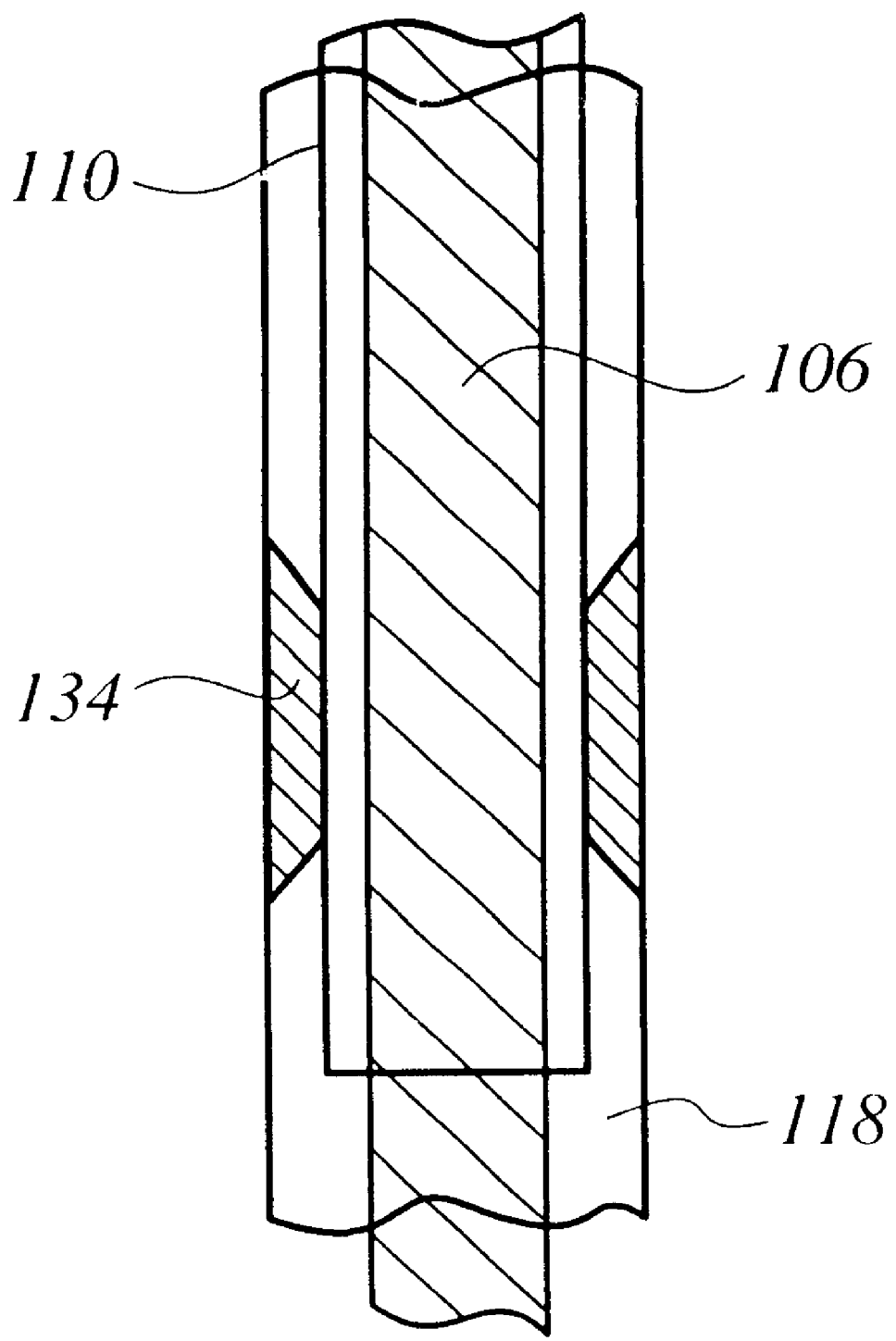
FIG. 2B is a schematic representation, on an enlarged scale of a portion of the reference junction shown in FIG. 2A.
Figure 2C:
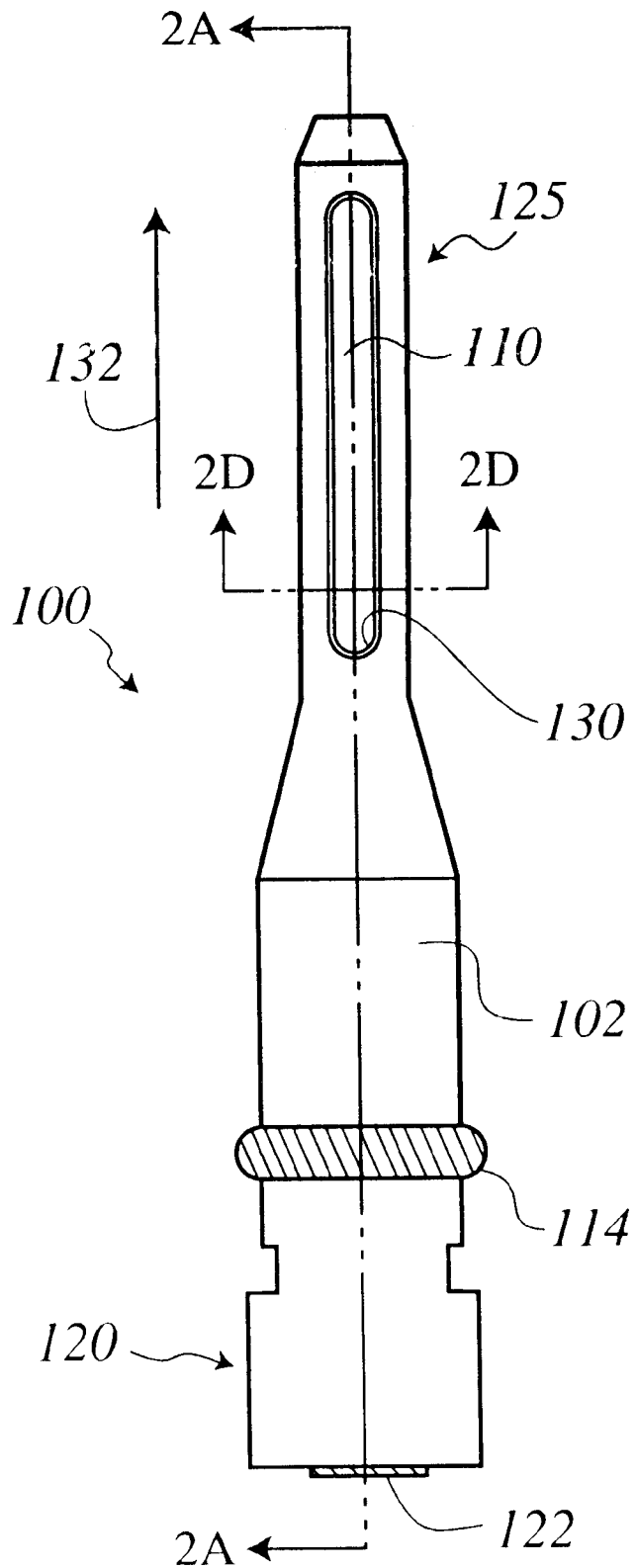
FIG. 2C is a schematic perspective view of the reference junction shown in FIG. 2A.
Figure 2D:
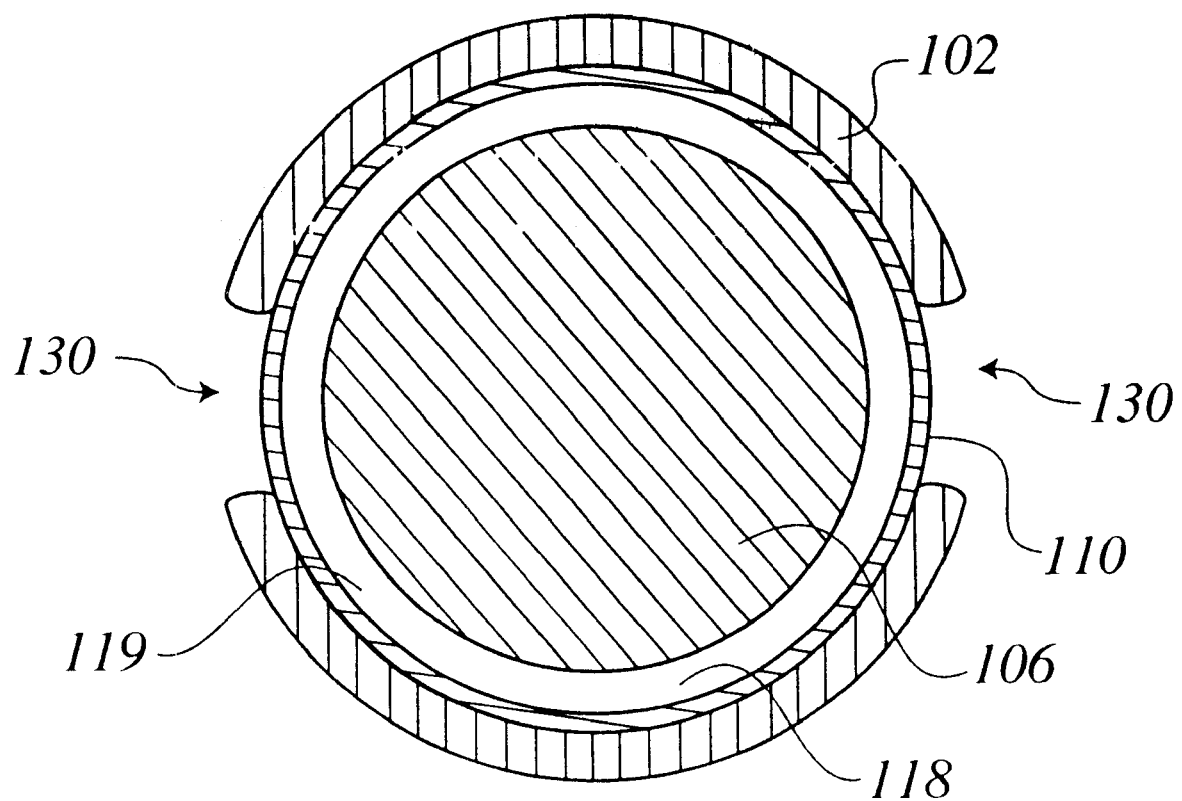
FIG. 2D is a cross-sectional view taken along 2D—2D of FIG. 2C.

Referring now to FIGS. 2C and 2D, one or more slots 130 provide an opening for electrical contact between the junction electrolyte 119 and reference electrolyte 42 (FIG. 1) included in a reference half-cell housing. Reference junction 100 may include one or more slots 130, typically positioned in symmetrical, circumferentially spaced locations, about the shaft-like body portion 102. Two slots 130 (as shown in FIG. 2D) have been found to be generally desirable, providing sufficient area for a relatively low resistance junction between electrolytes 42 (FIG. 1) and 119, while also enabling the body 102 to provide sufficient structural support and mechanical protection to ion-barrier membrane 110 to prevent damage thereto during field use and/or installation. Reference junction 100 thus provides for electrical continuity from plug 122, through junction electrolyte 119 disposed within cavity 118 (which may also include a wick 106), through membrane 110, and slot(s) 130 to a reference electrolyte 42 (FIG. 1).

During construction of an exemplary embodiment of reference junction 100, wick 106 may be inserted into the internal cavity 118. An ion-barrier membrane 110, in the form of a cylindrical tube, may be inserted into internal cavity 118 around wick 106 and a portion thereof pressed past a constriction member 134 (as shown in FIG. 2B), which in one embodiment is a portion of the internal cavity 118 having a reduced inner diameter. Reference junction 100 may then be filled with junction electrolyte 119 (e.g., potassium chloride) and sealed with a plug 126 (FIG. 2A). Plug 126 is typically a room temperature vulcanized (RTV) rubber. As stated hereinabove, the introduction of junction electrolyte 119 typically causes wick 106 to swell and press ion-barrier membrane tube into constriction member 134 (FIG. 2B), which effects a seal preventing direct fluid contact between the electrolytes 42 (FIG. 1) and 119.

Reference junction 100 may be constructed having substantially any dimensions. In general, the size of reference junction 100 may be configured to suit the needs of a particular application. In one embodiment, a reference junction 100 including a length dimension of from about 1.5 to about 2.5 inches with a slot 130 including a length dimension of from about 0.5 to about 1.0 inches is desirable.

Figure 3A:
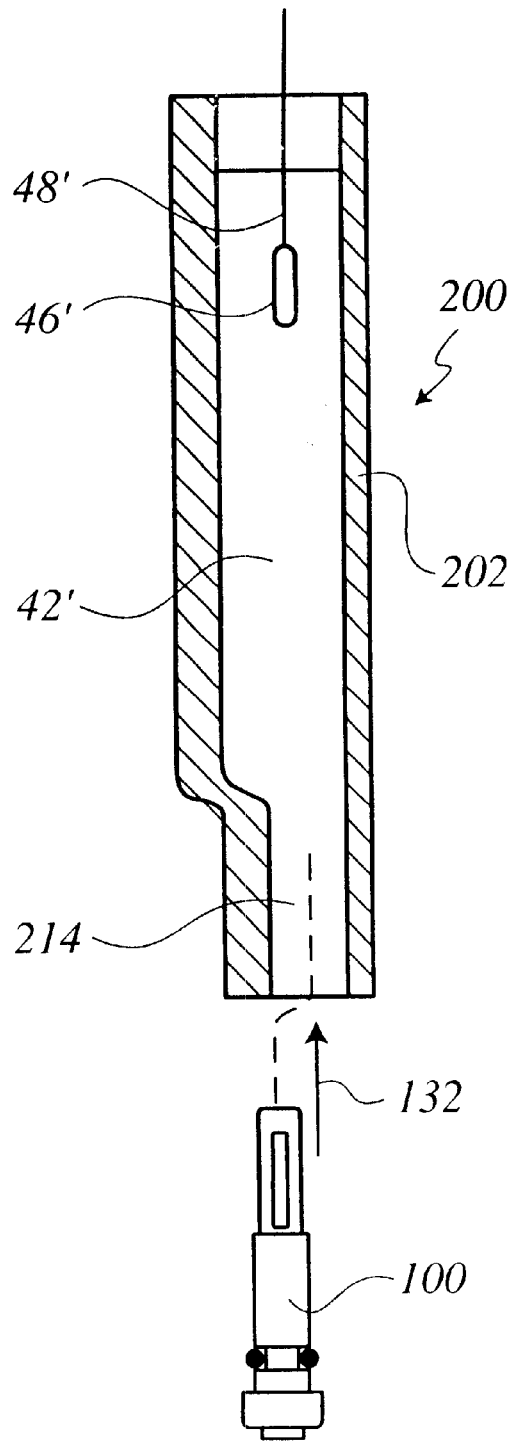
FIG. 3A is an exploded, partially cross-sectional schematic view of one embodiment of a reference half-cell including the reference junction of FIG. 2A.
Figure 3B:
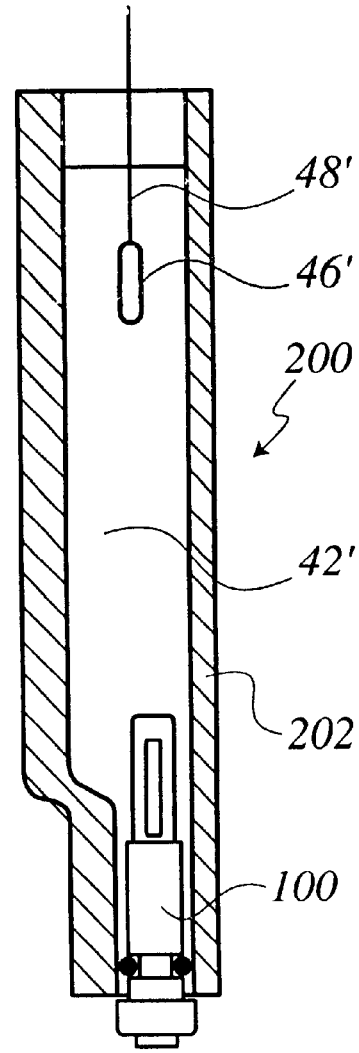
FIG. 3B is a partially cross-sectional schematic view of the reference half-cell of FIG. 3A with the reference junction inserted into the reference half-cell housing.

Referring now to FIGS. 3A and 3B, schematic representations of one embodiment of a reference half-cell 200 that incorporates reference junction 100 of this invention are illustrated. Reference half-cell 200 includes a half-cell electrode 46', a reference electrolyte 42 (FIG. 1)', and a reference junction 100 configured for selectively inserting and removing from an outlet 214 in the reference half-cell housing 202. FIG. 3A shows reference junction 100 removed from reference half-cell housing 202 and positioned for inserting into outlet 214, while FIG. 3B shows reference junction 100 inserted into housing 202. Half-cell electrode 46' may include substantially any electrode material. Typical electrode materials may include one or more of the following mercury-mercurous sulfate, mercury-mercurous chloride, silver—silver chloride, silver, or other redox couples known to those skilled in the art. Half-cell electrode 46' is coupled to an electrical connector 48', which is typically a silver wire or some other electrically conducting material. Reference electrolyte 42 (FIG. 1)' may include substantially any electrolyte solution. Typical electrolyte solutions may include one or more of the following potassium chloride, silver chloride, mixtures of silver chloride and potassium chloride, potassium sulfate, and methyl cyanide. A four molar potassium chloride solution saturated with silver chloride is a generally desirable reference electrolyte 42 (FIG. 1)' for use with a silver—silver chloride half-cell electrode 46'.

Figure 4A:
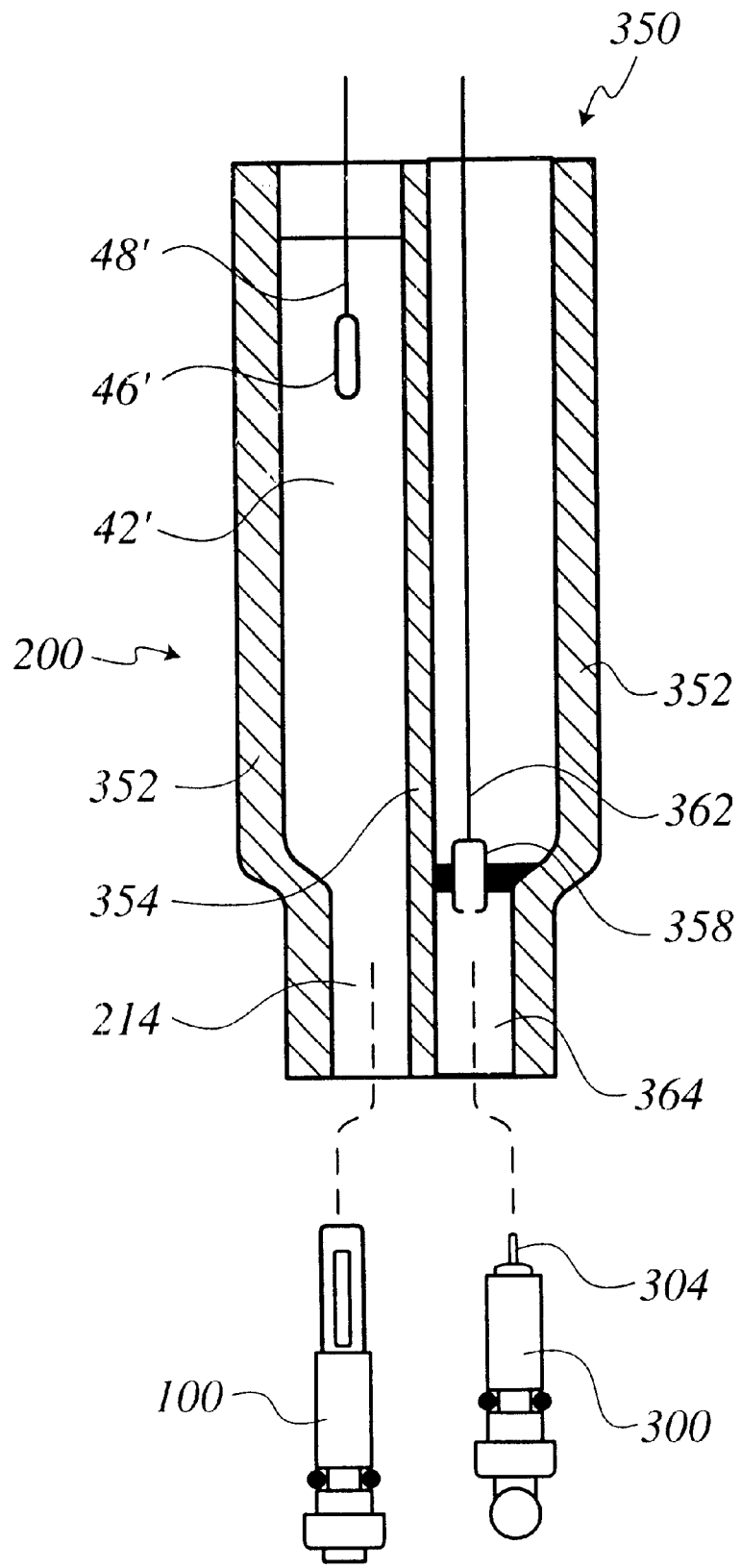
FIG. 4A is a view similar to that of FIG. 3A, of an electrochemical potential measurement sensor including the reference junction of FIG. 2A.
Figure 4B:
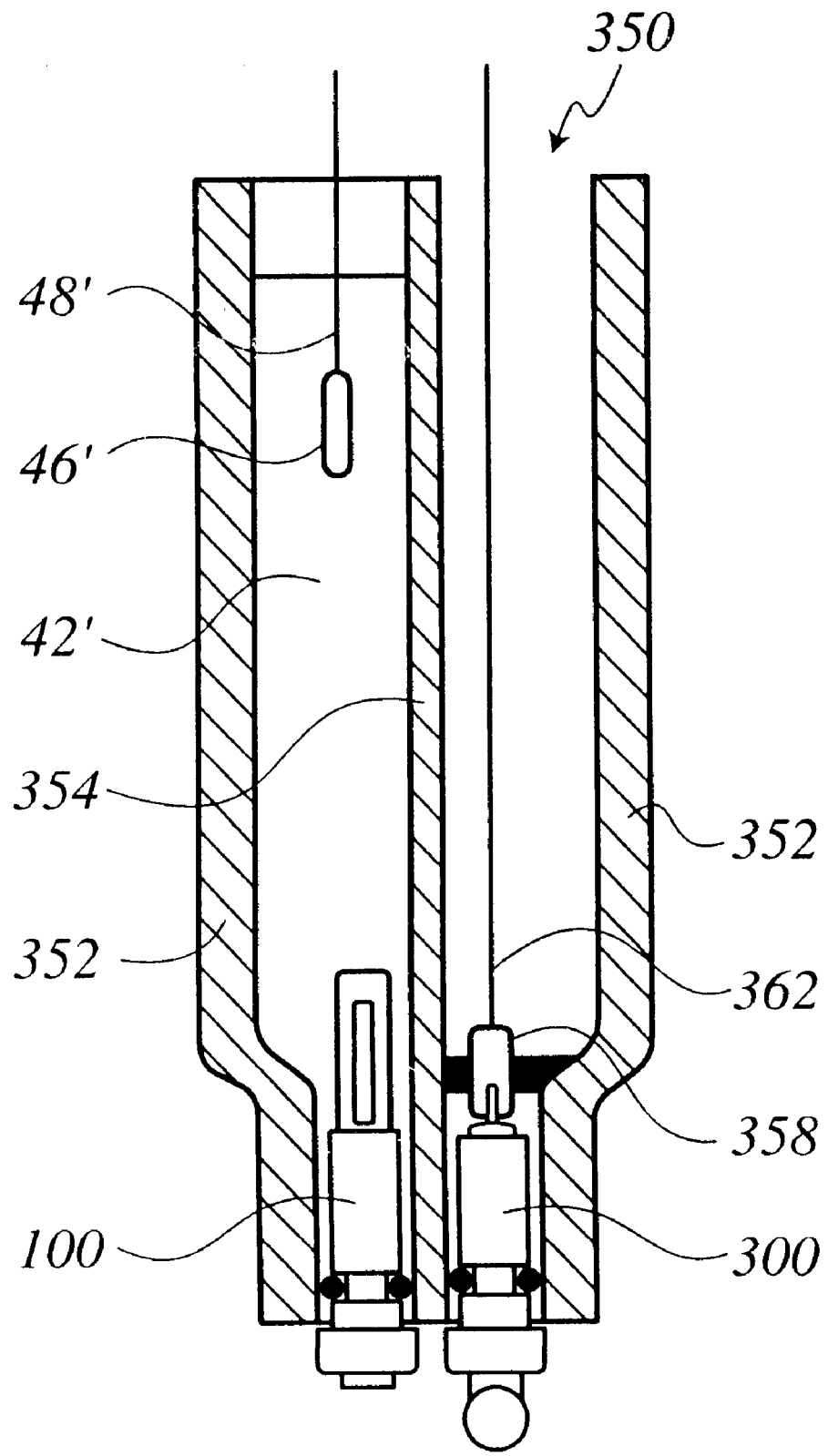
FIG. 4B is a view similar to that of FIG. 3B, of the electrochemical potential measurement sensor of FIG. 4A with the reference junction and measuring half-cell inserted into the sensor housing.

Referring now to FIGS. 4A and 4B, one embodiment of an electrochemical potential measurement sensor 350 of this invention is illustrated. Sensor 350 includes a sensor housing 352, which houses both a reference half-cell 200 and a measuring half-cell 300. A partition 354 within the sensor 350 divides the sensor into reference and measurement electrode portions. Measuring half-cell 300 is configured for selective insertion and removal from an opening 364 in a sensor housing 352. FIG. 4A shows both reference junction 100 and measuring half-cell 300 removed from sensor housing 352 and positioned for insertion into outlet 214 and opening 364, respectively, while FIG. 4B shows both reference junction 100 and measuring half-cell 300 inserted into sensor housing 352. Measuring half-cell 300 typically includes an electrical connector 304, which makes contact with a jack 358 when measuring half-cell 300 is inserted into sensor housing 352. Jack 358 is electrically connected to a lead wire 362. Measuring half-cell 300 may include any electrode useful for making electrochemical potential measurements. In one embodiment, measuring half-cell 300 includes a pH electrode. In another embodiment, measuring half-cell 300 includes another type of selective ion electrode, such as a selective fluoride ion electrode. In yet another embodiment, measuring half-cell 300 includes an oxidation-reduction potential (ORP) electrode. Further, sensor 350 may be equipped with optional fittings or accessories such as bushings, tees, sleeves, and the like for convenient mounting to piping, various processing and/or storage tanks, as well as other industrial vessels of substantially any kind.

The modifications to the various aspects of the present invention described hereinabove are merely exemplary. It is understood that other modifications to the illustrative embodiments will readily occur to persons with ordinary skill in the art. All such modifications and variations are deemed to be within the scope and spirit of the present invention as defined by the accompanying claims.

What we claim is:

1. A modular reference junction for a reference half-cell, said reference junction comprising:
   a body including a reference electrolyte interface portion and a process solution interface portion;
   the body defining an internal cavity;
   the process solution interface portion including a porous plug disposed in a recess of the body;
   the reference electrolyte interface portion having at least one opening extending from the internal cavity to a reference junction exterior;
   a wick disposed in the internal cavity;
   a junction electrolyte disposed in the internal cavity in contact with the wick;
   an ion-barrier membrane disposed in the internal cavity between the wick and a membrane engagement portion of the body;
   the wick being sized and shaped to apply pressure against the ion-barrier membrane to seal the ion-barrier membrane against the membrane engagement portion of the body;
   wherein the at least one opening is disposed on one side of the ion-barrier membrane, and the porous plug is disposed on the other side of the ion-barrier membrane; and
   an electrical path of least resistance through the reference junction is provided from the reference electrolyte interface portion, through the ion-barrier membrane, through the junction electrolyte, and to the process solution interface portion.

2. The reference junction of claim 1 wherein said body comprises plastic.

3. The reference junction of claim 1 wherein said body includes a taper.

4. The reference junction of claim 1 wherein said internal cavity is substantially cylindrically shaped.

5. The reference junction of claim 1 wherein the membrane engagement portion of the body includes a portion of the body having a reduced inner dimension.

6. The reference junction of claim 1 wherein said internal cavity is substantially filled with a junction electrolyte.

7. The reference junction of claim 6 wherein said junction electrolyte comprises a potassium chloride solution.

8. The reference junction of claim 7 wherein said junction electrolyte comprises a four molar potassium chloride solution.

9. The reference junction of claim 1, wherein said opening comprises two elongated slots, said slots having a length of from about 0.5 to about 1.0 inches.

10. The reference junction of claim 1 wherein said ion-barrier membrane is disposed in said internal cavity in superposition with said opening.

11. The reference junction of claim 1 wherein said ion-barrier membrane comprises a cylindrical tube.

12. The reference junction of claim 1 wherein said ion-barrier membrane comprises an ionic exchange film.

13. The reference junction of claim 1 wherein said ion-barrier membrane comprises a cationic exchange film.

14. The reference junction of claim 1 wherein said ion-barrier membrane comprises a member of the group consisting of polystyrene sulfonic acid, polyacrylic acid, polymethacrylic acid, and poly(perfluorosulfonic acid).

15. The reference junction of claim 14 wherein said ion-barrier membrane comprises poly(perfluorosulfonic acid).

16. The reference junction of claim 1 wherein said wick comprises paper.

17. The reference junction of claim 1 wherein said wick effects a seal between said ion-barrier membrane and a portion of said body having a reduced inner diameter.

18. The reference junction of claim 1 wherein said porous plug comprises a porous ceramic.

19. The reference junction of claim 1 having a length of from about 1.5 to about 2.5 inches.

20. A reference half-cell comprising:
   a half-cell electrode;
   a reference electrolyte;
   a reference junction positioned in an outlet for said reference electrolyte;
   said reference junction being sized and shaped for removable receipt within said outlet; and
   said reference junction including a body having a reference electrolyte interface portion and a process solution interface portion;
   the body defining an internal cavity;
   the process solution interface portion including a porous plug disposed in a recess of the body;
   the reference electrolyte interface portion having at least one opening extending from the internal cavity to a reference junction exterior;
   a wick disposed in the internal cavity;
   a junction electrolyte disposed in the internal cavity in contact with the wick;
   an ion-barrier membrane disposed in the internal cavity between the wick and a membrane engagement portion of the body;
   the wick being sized and shaped to apply pressure against the ion-barrier membrane to seal the ion-barrier membrane against the membrane engagement portion of the body;
   wherein the at least one opening is disposed on one side of the ion-barrier membrane, and the porous plug is disposed on the other side of the ion-barrier membrane; and
   an electrical path of least resistance through the reference junction is provided from the reference electrolyte interface portion, through the ion-barrier membrane, through the junction electrolyte, and to the process solution interface portion.

21. The reference half-cell of claim 20 wherein said half-cell electrode comprises a member of the group consisting of silver, silver—silver chloride, mercury-mercurous sulfate, mercury-mercurous chloride, and other redox couples.

22. The reference half-cell of claim 20 wherein said half-cell electrode comprises silver—silver chloride.

23. The reference half-cell of claim 20 wherein said reference electrolyte comprises a member of the group consisting of potassium chloride, silver chloride, mixtures of silver chloride and potassium chloride, potassium sulfate, and methyl cyanide.

24. The reference half-cell of claim 20 wherein said reference electrolyte comprises a mixture of silver chloride and potassium chloride.

25. The reference half-cell of claim 24 wherein said reference electrolyte comprises a mixture of about 4 molar potassium chloride and saturated silver chloride.

26. The reference half-cell of claim 20 wherein said ion-barrier membrane comprises a cationic exchange film.

27. The reference half-cell of claim 20 wherein said ion-barrier membrane comprises a film including poly (perfluorosulfonic acid).

28. An electrochemical potential measurement sensor comprising:

a measuring half-cell;

a reference half-cell including a half-cell electrode, a reference electrolyte, and a reference junction positioned in an outlet for said reference electrolyte;

said reference junction being sized and shaped for removable receipt within said outlet;

said reference junction including a body having a reference electrolyte interface portion and a process solution interface portion;

the body defining an internal cavity;

the process solution interface portion including a porous plug disposed in a recess of the body;

the reference electrolyte interface portion having at least one opening extending from the internal cavity to a reference junction exterior;

a wick disposed in the internal cavity;

a junction electrolyte disposed in the internal cavity in contact with the wick;

an ion-barrier membrane disposed in the internal cavity between the wick and a membrane engagement portion of the body;

the wick being sized and shaped to apply pressure against the ion-barrier membrane to seal the ion-barrier membrane against the membrane engagement portion of the body;

wherein the at least one opening is disposed on one side of the ion-barrier membrane, and the porous plug is disposed on the other side of the ion-barrier membrane; and an electrical path of least resistance through the reference junction is provided from the reference electrolyte interface portion, through the ion-barrier membrane, through the junction electrolyte, and to the process solution interface portion.

29. The sensor of claim 28 wherein said measuring half-cell and said reference half-cell are mounted in a common housing.

30. The sensor of claim 28 wherein said measuring half-cell comprises a pH electrode.

31. The sensor of claim 28 wherein said measuring half-cell comprises a selective ion electrode.

32. The sensor of claim 28 wherein said measuring half-cell comprises a fluoride ion selective electrode.

33. The sensor of claim 28 wherein said measuring half-cell comprises an oxidation-reduction potential electrode.

34. The sensor of claim 28 wherein said measuring half-cell is sized and shaped for removable insertion into a sensor housing.

35. The sensor of claim 28 wherein said ion-barrier membrane comprises poly(perfluorosulfonic acid).

36. A method for measuring electrochemical potential comprising:

providing a reference half-cell including a half-cell electrode, a reference electrolyte, and the reference junction of claim 1, positioned in an outlet for said reference electrolyte, said reference junction being sized and shaped for removable insertion into said outlet;

providing a measuring half-cell;

inserting said reference half-cell and said measuring half-cell into a liquid;

electrically connecting said reference half-cell and said measuring half-cell to a voltage meter;

using the voltage meter to generate a total voltage value; and subtracting the potential of the reference half-cell from the total voltage value.

37. A method for fabricating a reference junction for a reference half-cell, said method comprising:

providing a body including a reference electrolyte interface portion and a process solution interface portion, the body defining an internal cavity;

disposing a porous plug in a recess of the process solution interface portion of the body;

providing an opening in the reference electrolyte interface portion extending from the internal cavity to a reference junction exterior;

disposing a wick in the internal cavity;

disposing a junction electrolyte in the internal cavity in contact with the wick;

disposing an ion-barrier membrane in the internal cavity between the wick and a membrane engagement portion of the body;

sizing and shaping the wick to apply pressure against the ion-barrier membrane to seal the ion-barrier membrane against the membrane engagement portion of the body;

wherein the at least one opening is disposed on one side of the ion-barrier membrane, and the porous plug is disposed on the other side of the ion-baffler membrane; and an electrical path of least resistance through the reference junction is provided from the reference electrolyte interface portion, through the ion-barrier membrane, through the junction electrolyte, and to the process solution interface portion.

* * * * *